US011730713B2

(12) United States Patent
Suga et al.

(10) Patent No.: US 11,730,713 B2
(45) Date of Patent: Aug. 22, 2023

(54) COMPOSITION FOR PREVENTING OR IMPROVING NOCICEPTIVE PAIN

(71) Applicant: AJINOMOTO CO., INC., Tokyo (JP)

(72) Inventors: Yasuyo Suga, Kawasaki (JP); Ikuko Sasahara, Kawasaki (JP); Masaki Hashimoto, Tokyo (JP); Tomoyuki Mine, Tokyo (JP); Michihiro Takada, Kawasaki (JP); Makoto Ishii, Kawasaki (JP); Michiya Kanzaki, Tokyo (JP)

(73) Assignee: AJINOMOTO CO., INC., Tokyo (JP)

( * ) Notice: Subject to any disclaimer, the term of this patent is extended or adjusted under 35 U.S.C. 154(b) by 150 days.

(21) Appl. No.: 16/936,799

(22) Filed: Jul. 23, 2020

(65) Prior Publication Data

US 2020/0345677 A1    Nov. 5, 2020

Related U.S. Application Data

(63) Continuation of application No. PCT/JP2019/002387, filed on Jan. 25, 2019.

(30) Foreign Application Priority Data

Jan. 26, 2018  (JP) ................................. 2018-011964

(51) Int. Cl.
| | |
|---|---|
| *A61K 31/202* | (2006.01) |
| *A23L 33/12* | (2016.01) |
| *A23L 33/175* | (2016.01) |
| *A61P 25/04* | (2006.01) |
| *A61K 9/00* | (2006.01) |
| *A61K 31/198* | (2006.01) |

(52) U.S. Cl.
CPC ............ *A61K 31/202* (2013.01); *A23L 33/12* (2016.08); *A23L 33/175* (2016.08); *A61K 9/0056* (2013.01); *A61K 31/198* (2013.01); *A61P 25/04* (2018.01); *A23V 2002/00* (2013.01)

(58) Field of Classification Search
None
See application file for complete search history.

(56) References Cited

U.S. PATENT DOCUMENTS

| | | |
|---|---|---|
| 2004/0192615 A1 | 9/2004 | Hageman |
| 2005/0192352 A1 | 9/2005 | Caterson et al. |
| 2017/0035721 A1* | 2/2017 | Mine .................. A61P 43/00 |

FOREIGN PATENT DOCUMENTS

| | | | |
|---|---|---|---|
| JP | 2005-529980 A | 10/2005 | |
| JP | 2015-91817 A | 5/2015 | |
| WO | WO 2015/142702 A1 | 9/2015 | |
| WO | WO 2015/163316 * | 10/2015 | ........... A61K 31/198 |
| WO | WO 2015/163316 A1 | 10/2015 | |
| WO | WO 2016/152054 A1 | 9/2016 | |

OTHER PUBLICATIONS

MD Biosciences (Nociception, Neuropathic and Inflammatory Pain, available online at https://www.mdbiosciences.com/hs-fs/hub/42723/file-5409230-pdf/docs/nociception-neuropathic-inflammatory_pain.pdf, accessed Jul. 1, 2022) (Year: 2022).*
Charles River (Pain Studies, available online at https://www.criver.com/products-services/discovery-services/pharmacology-studies/neuroscience-models-assays/pain-studies?region=3601, accessed Jul. 1, 2022) (Year: 2022).*
Schnitzer et al. (Molecular Pain 12:1-8, 2016) (Year: 2016).*
Shell et al. (Am J Therapeut e1353-e1362, 2016) (Year: 2016).*
Spahr et al (Musculoskeletal Science & Practice 27:40-48, 2017) (Year: 2017).*
Theramine Product Information sheet (available online at https://mrsrelief.com/sites/default/files/medical-foods-files/Theramine_Package_Insert_June_2015.pdf) (Year: 2015).*
Extended European Search Report dated Dec. 1, 2021 in European Patent Application No. 19743131.5, citing documents AM, AN and AV-AX therein, 12 pages.
Masanobu Yoshikawa, et al., "Activation of Supraspinal NMDA Receptors by both D-Serine Alone or in Combination with Morphine Leads to the Potentiation of Antinociception in Tail-Flick Test of Rats" European Journal of Pharmacology, vol. 565, No. 1-3, XP55862293, Jun. 1, 2007, pp. 89-97.
T. Kiya, et al., "Role of Satellite Cell-Derived 1-Serine in the Dorsal Root Ganglion in Paclitaxel-Induced Painful Peripheral Neuropathy" Neuroscience, New York, NY, US, vol. 174, XP027589595, Feb. 3, 2011, pp. 190-199.
Akihiko Hiyama, et al., "Evaluation of Quality of Life and Neuropathic Pain in Patients with Low Back Pain Using the Japanese Orthopedic Association Back Pain Evaluation Questionnaire" European Spine Journal, Springer Berlin Heidelberg, vol. 24, No. 3, XP035473341, Dec. 14, 2014, pp. 503-512.
Yabuki, S., et al., "a Nationwide Survey of Chronic Pain Sufferers in Japan", Clinical Orthopedic Surgery, vol. 47, No. 2, 2012, pp. 127-134 (with English abstract).
Watanabe, M., et al., "Mechanisms of pain and pain relief", Journal of Allied Health Sciences, vol. 8, No. 1, 2017, pp. 50-63 (with English abstract).
Jeong, Y. C. et al., "Inhibition of Mitogen-Activated Protein Kinases Phosphorylation Plays an Important Role in the Anti-nociceptive Effect of Pregabalin in Zymosan-Induced Inflammatory Pain Model", Biological and Pharmaceutical Bulletin, 2014, vol. 37, No. 10, pp. 1694-1698.
Guerrero, A. T. G., et al., "Toll-like receptor 2/MyD88 signaling mediates zymosan-induced joint hypernociception in mice: Participation of TNF-α, IL-1β and CXCL1/KC", European Journal of Pharmacology, 2012, vol. 674, No. 1, pp. 51-57.

(Continued)

*Primary Examiner* — Craig D Ricci
(74) *Attorney, Agent, or Firm* — Oblon, McClelland, Maier & Neustadt, L.L.P.

(57) ABSTRACT

Compositions which contain an amino acid comprising serine, and a lipid comprising at least one n-3 fatty acid are useful for preventing or improving nociceptive pain.

5 Claims, No Drawings

(56) References Cited

OTHER PUBLICATIONS

Alves, S. M., et al., "Anti-inflammatory and anti-nociceptive effects of strontium ranelate on the zymosan-induced temporomandibular joint inflammatory hypernociception in rats depend on TNF-α inhibition", Pharmacological Reports, 2017, vol. 69, No. 4, pp. 764-772.

Ito, M., et al., "Antinociceptive effect of intracerebroventricular administration or D-serine on formalin-induced pain", Journal of Anesthesia, 2014, vol. 28, No. 2, pp. 228-234.

Ito, K., et al., "Midazolam attenuated the antinociceptive effect of D-serine and morphine at supraspinal level", Journal of Pharmacological Sciences, 2007, vol. 103, no. Supplement, p. 236P.

Nakamoto, K., et al., "Antinociceptive Effects of Docosahexaenoic Acid against Various Pain Stimuli in Mice", Biological and Pharmaceutical Bulletin, 2010, vol. 33, No. 6, pp. 1070-1072.

Nobre, M. E. P., et al., "Eicosapentaenoic acid and docosahexaenoic acid exert anti-inflammatory and antinociceptive effects in rodents at low doses", Nutrition Research, 2013, vol. 33, No. 5, pp. 422-433.

\* cited by examiner

COMPOSITION FOR PREVENTING OR IMPROVING NOCICEPTIVE PAIN

CROSS REFERENCES TO RELATED APPLICATIONS

This application is a continuation of International Patent Application No. PCT/JP2019/002387, filed on Jan. 25, 2019, and claims priority to Japanese Patent Application No. 2018-011964, filed on Jan. 26, 2018, both of which are incorporated herein by reference in their entireties.

BACKGROUND OF THE INVENTION

Field of the Invention

The present invention relates to compositions for preventing or improving nociceptive pain, which contain serine and n-3 fatty acid as active ingredients. The present invention also relates to methods for preventing or improving nociceptive pain.

Discussion of the Background

Pain is classified into "neuropathic", "nociceptive" and "psychogenic", and these three act independently or compositely to cause a pain. Pain includes acute pain and chronic pain, and acute pain that follows damage on the body tissues functions as an alert of body tissue damage, and leads to the repair of the body tissue in a given period. On the other hand, a chronic pain does not act as a defensive biological function, and is considered to last for several months to several years or longer (see Neurological Therapeutics, vol. 27, No. 4, p591-622 (2010), which is incorporated herein by reference in its entirety).

According to a major research relating to pain, about 23% of the Japanese adults have a chronic pain, and 70% thereof fail to appropriately alleviate the pain (see Clinical Orthopaedic Surgery, vol. 47, No. 2, p127-134 (2012), which is incorporated herein by reference in its entirety). Since psychological anxiety and melancholiness associated with pain have a high impact on the limitation of activity, removal of pain improves quality of life.

Peripheral neuropathy has conventionally been reported to be prevented or improved by a composition containing serine and n-3 fatty acid (see WO 2015/163316, which is incorporated herein by reference in its entirety). However, it has not been reported that nociceptive pain with a completely different mechanism of development from peripheral neuropathy can be prevented or improved by a composition containing serine and n-3 fatty acid. As a therapeutic drug for nociceptive pain, non-steroidal antiinflammatory drugs (NSAIDs), steroidal antiinflammatory agents or the like are used (see Journal of Allied Health Sciences, vol.8, No.1, p50-63 (2017), which is incorporated herein by reference in its entirety). However, pain often relapses when the use is discontinued, even though analgesic effects are shown during use. On the other hand, long-term use of these medicaments is associated with risk due to side effects and drug resistance, and existing therapeutic drugs are not sufficient in terms of both efficacy and safety.

SUMMARY OF THE INVENTION

Accordingly, it is one object of the present invention to provide a composition having a prophylactic or improvement effect on nociceptive pain.

It is another object of the present invention to provide novel methods of preventing or treating nociceptive pain.

These and other objects, which will become apparent during the following detailed description, have been achieved by the inventors' discovery that nociceptive pain can be prevented or improved by using serine and n-3 fatty acid in combination.

Therefore, the present invention is as described below.

(1) A composition for preventing or improving nociceptive pain, which composition comprises an amino acid comprising serine, and a lipid comprising a n-3 fatty acid.
(2) The composition of (1), wherein the n-3 fatty acid comprises one or more kinds selected from the group consisting of eicosapentaenoic acid, docosapentaenoic acid and docosahexaenoic acid.
(3) The composition of (1) or (2), wherein the amount of serine is not less than 50 wt % relative to the total amount of amino acid.
(4) The composition of any one of (1) to (3), wherein the composition is (1) substantially free of threonine, or has (2) a weight ratio of serine relative to threonine of not less than 2.60.
(5) The composition of any one of (1) to (4), wherein the amount of n-3 fatty acid is not less than 20 wt % relative to the total amount of the lipid.
(6) The composition of any one of (1) to (5), wherein the composition has a unit package form per single intake, and comprises not less than 0.1 g of serine in one unit, and not less than 0.03 g of n-3 fatty acid in one unit.
(7) The composition of any one of (1) to (6), wherein the nociceptive pain is a nociceptive pain in a joint or limb.
(8) The composition of any one of (1) to (7), wherein the composition is a medicament or food.
(9) A composition for preventing or improving a decrease in QOL associated with nociceptive pain, which composition comprises an amino acid comprising serine, and a lipid comprising a n-3 fatty acid.
(10) A method for preventing or improving nociceptive pain, comprising administering an effective amount of a composition comprising an amino acid comprising serine, and a lipid comprising a n-3 fatty acid to a subject in need thereof.
(11) The method of (10), wherein the n-3 fatty acid comprises one or more kinds selected from the group consisting of eicosapentaenoic acid, docosapentaenoic acid and docosahexaenoic acid.
(12) The method of (10) or (11), wherein the amount of serine contained in the aforementioned composition is not less than 50 wt % relative to the total amount of amino acid in the composition.
(13) The method of any of (10) to (12), wherein (1) the aforementioned composition is substantially free of threonine, or (2) the aforementioned composition has a weight ratio of serine relative to threonine of not less than 2.60.
(14) The method of any one of (10) to (13), wherein the amount of n-3 fatty acid contained in the aforementioned composition is not less than 20 wt % relative to the total amount of the lipid in the composition.
(15) The method of any one of (10) to (14), wherein the aforementioned composition has a unit package form per single intake, comprises not less than 0.1 g of serine in one unit, and not less than 0.03 g of n-3 fatty acid in one unit.
(16) The method of any one of (10) to (15), wherein the nociceptive pain is a nociceptive pain in a joint or limb.
(17) The method of any one of (10) to (16), wherein the aforementioned composition is a medicament or food.

(18) A method for preventing or improving a decrease in QOL associated with nociceptive pain, comprising administering an effective amount of a composition comprising an amino acid comprising serine, and a lipid comprising a n-3 fatty acid to a subject in need thereof.
(19) A composition comprising an amino acid comprising serine, and a lipid comprising a n-3 fatty acid, which is for use for preventing or improving nociceptive pain.
(20) The composition of (19), wherein the n-3 fatty acid comprises one or more kinds selected from the group consisting of eicosapentaenoic acid, docosapentaenoic acid and docosahexaenoic acid.
(21) The composition of (19) or (20), wherein the amount of serine is not less than 50 wt % relative to the total amount of amino acid.
(22) The composition of any one of (19) to (21), wherein the composition is (1) substantially free of threonine, or has (2) a weight ratio of serine relative to threonine of not less than 2.60.
(23) The composition of any one of (19) to (22), wherein the amount of n-3 fatty acid is not less than 20 wt % relative to the total amount of the lipid.
(24) The composition of any one of (19) to (23), wherein the composition has a unit package form per single intake, and comprises not less than 0.1 g of serine in one unit, and not less than 0.03 g of n-3 fatty acid in one unit.
(25) The composition of any one of (19) to (24), wherein the nociceptive pain is a nociceptive pain in a joint or limb.
(26) The composition of any one of (19) to (25), wherein the composition is a medicament or food.
(27) A composition comprising an amino acid comprising serine, and a lipid comprising a n-3 fatty acid, which is for use for preventing or improving a decrease in QOL associated with nociceptive pain.
(28) Use of a composition comprising an amino acid comprising serine, and a lipid comprising a n-3 fatty acid for producing an agent for preventing or improving nociceptive pain.
(29) The use of (28), wherein the n-3 fatty acid comprises one or more kinds selected from the group consisting of eicosapentaenoic acid, docosapentaenoic acid and docosahexaenoic acid.
(30) The use of (28) or (29), wherein the amount of serine contained in the aforementioned composition is not less than 50 wt % relative to the total amount of amino acid.
(31) The use of any one of (28) to (30), wherein (1) the aforementioned composition is substantially free of threonine, or (2) has a weight ratio of serine of not less than 2.60 relative to threonine in the aforementioned composition.
(32) The use of any one of (28) to (31), wherein the amount of n-3 fatty acid contained in the aforementioned composition is not less than 20 wt % relative to the total amount of the lipid.
(33)] The use of any one of (28) to (32), wherein the aforementioned composition has a unit package form per single intake, and comprises not less than 0.1 g of serine in one unit, and not less than 0.03 g of n-3 fatty acid in one unit.
(34) The use of any one of (28) to (33), wherein the nociceptive pain is a nociceptive pain in a joint or limb.
(35) The use of any one of (28) to (34), wherein the aforementioned composition is a medicament or food.
(36) Use of a composition comprising an amino acid comprising serine, and a lipid comprising a n-3 fatty acid for the production of a prophylactic or improving agent for decrease in QOL associated with nociceptive pain.

Advantageous Effects of Invention

According to the present invention, a composition for preventing or improving nociceptive pain can be provided.

According to the present invention, a composition for preventing or improving a decrease in QOL (Quality of Life) associated with nociceptive pain can be provided.

Furthermore, since the composition contains serine and a n-3 fatty acid with established safety as active ingredients, it can be ingested safely for a long term.

DETAILED DESCRIPTION OF THE PREFERRED EMBODIMENTS

The composition for preventing or improving nociceptive pain of the present invention (hereinafter to be also simply referred to as "the composition of the present invention") is mainly characterized in that it contains an amino acid comprising serine, and a lipid comprising a n-3 fatty acid.

Amino Acid Containing Serine

An amino acid used in the present invention essentially contains serine. The form of serine is not particularly limited, and may be a free form, as well as a form that can produce free serine by enzymatic reaction, hydrolysis, or the like in vivo (e.g., amino acid constituting peptide, amino acid constituting protein, etc.). When free serine is used, it may be a salt or any form of the solvated thereof, or a mixture of these.

Examples of the salt of serine include acid addition salt, salt with base and the like, and a physiologically acceptable salt is preferable.

Examples of the acid that forms a physiologically acceptable salt of serine include inorganic acids such as hydrogen chloride, hydrogen bromide, sulfuric acid, phosphoric acid and the like; and organic acids such as acetic acid, lactic acid, citric acid, tartaric acid, maleic acid, fumaric acid, monomethyl sulfuric acid and the like.

Examples of the base that forms a physiologically acceptable salt of serine include inorganic bases such as hydroxide or carbonate of metal (e.g., sodium, potassium, calcium etc.), ammonia and the like; and organic bases such as ethylenediamine, propylenediamine, ethanolamine, monoalkylethanolamine, dialkylethanolamine, diethanolamine, triethanolamine and the like.

A salt of only one kind of these salts or two or more kinds of salts in combination may be used.

Serine in a free form to be used in the present invention may be any of L-form, D-form and DL-form, and L-form is preferable.

The production method of serine is not particularly limited, and a method known per se (e.g., protein hydrolysis method, chemical synthesis method, enzyme method, fermentation method etc.) can be used for production. A commercially available product may also be used. Serine can also be obtained by enzymatic hydrolysis of an animal or plant-derived natural protein having an amino acid sequence containing the serine residue.

The amino acid contained in the composition of the present invention may be composed of serine alone. The composition of the present invention may contain, in addition to serine, an amino acid other than serine (e.g., threonine, glycine etc.). The form of these amino acids is not particularly limited, and may be a free form and a salt thereof, or a form of peptide wherein two or more amino acids are linked by a peptide bond. Also, it may have a form of a protein, and examples of the protein include animal-derived protein (e.g., casein, acid casein, casein sodium, casein calcium, whey protein, milk serum whey protein, fish meat protein, egg protein, and these hydrolysate etc.) and plant-derived protein (e.g., soybean protein, wheat protein, corn protein, and these hydrolysate etc.) and the like. The amino acid to be used for the composition of the present invention may be any of L-form, D-form and DL-form.

The amount of serine in the composition of the present invention is preferably not less than 50 wt %, more preferably not less than 70 wt %, particularly preferably not less than 90 wt %, relative to the total amount of amino acid. The amount of serine in the composition of the present invention is calculated as a total weight of serine in any form contained in the composition of the present invention. When the form of serine is other than a free form, for example, salt or amino acid constituting peptide and protein, or the like, the weight of the serine is converted to the weight of a free form. The "total amount of amino acid" is calculated as a total weight of amino acid in any form (e.g., free amino acid and a salt thereof, peptide, protein etc.) contained in the composition of the present invention. When the form of amino acid is other than a free form, for example, salt or peptide and protein, or the like, the weight of the amino acid is converted to the weight of a free form.

The upper limit of the amount of serine in the composition of the present invention is not particularly set.

When the amino acid used in the present invention contains threonine, the weight ratio of serine to threonine (serine/threonine) is preferably not less than a particular value. When the weight ratio of serine to threonine (serine/threonine) is not less than a particular value, the composition of the present invention can exhibit a desired effect (e.g., nociceptive pain relieving effect etc.) sufficiently.

Specifically, the weight ratio of serine to threonine (serine/threonine) is preferably not less than 2.60, more preferably not less than 5.20, particularly preferably not less than 10.40.

The weight ratio of serine to threonine (serine/threonine) is a value obtained by dividing the amount of serine in the composition of the present invention by the amount of threonine in the present invention. The amount of threonine in the composition of the present invention is calculated as a total weight of threonine in any form contained in the composition of the present invention. When the form of threonine is other than a free form, for example, salt or amino acid constituting peptide and protein, or the like, the weight of the threonine is converted to the weight of a free form.

The weight ratio of serine and threonine (serine/threonine) contained in 100 g of a food edible part in a natural food material is shown in the following Table 1 (calculated based on "STANDARD TABLES OF FOOD COMPOSITION IN JAPAN: AMINO ACID COMPOSITION OF FOODS 2010" (the Subdivision on Resources, the Council for Science and Technology, Ministry of Education, Culture, Sports, Science and Technology, Japan)). As shown in Table 1, a food having a weight ratio of serine to threonine (serine/threonine) of not less than 2.60 cannot be realized with a natural food material. Such food requires addition of, for example, serine in a free form and the like to a natural food material.

TABLE 1

|  | serine/threonine |
|---|---|
| raw milk (Holstein) | 1.15 |
| rice (milled rice) | 1.48 |

TABLE 1-continued

|  | serine/threonine |
|---|---|
| sweet potato (tuberous root, raw) | 0.97 |
| soybean (dried) | 1.33 |
| onions (bulb, raw) | 1.50 |
| apples (raw) | 1.20 |
| Shiitake mushroom (raw) | 0.92 |
| Wakame (salted) | 0.89 |
| jack mackerel (raw) | 0.85 |
| pacific saury (raw) | 0.90 |
| Shiba shrimp (raw) | 0.94 |
| beef, comminuted meat (raw) | 0.85 |
| pork, comminuted meat (raw) | 0.89 |
| chicken, leg (with skin, raw) | 0.92 |
| egg of hen, whole egg (raw) | 1.57 |

The upper limit of the weight ratio of serine to threonine (serine/threonine) is not particularly limited, a smaller amount of threonine is more preferable, and the composition of the present invention is most preferably substantially free of threonine. The weight ratio of threonine to serine (threonine/serine, i.e., value obtained by dividing the amount of threonine in the composition of the present invention by the amount of serine in the present invention) is preferably not more than 0.38, more preferably not more than 0.20, particularly preferably not more than 0.10, most preferably 0. Being "substantially free of" threonine here means either (a) completely free of threonine, or (b) containing threonine in an amount not influential on the effect of the composition of the present invention (e.g., not more than 1 wt %, preferably not more than 0.1 wt %, relative to the total amount of amino acid).

In addition, since even threonine taken from a meal and the like (e.g., threonine contained in protein etc.) may influence the effect of the composition of the present invention, ingestion of the composition of the present invention and the ingestion of threonine (e.g., a meal etc.) are preferably at least 1 hour (preferably not less than 2 hours) apart.

The total amount amino acid contained in the composition of the present invention is generally 1 to 90 wt %, preferably 5 to 85 wt %, relative to the whole composition.

Lipid Containing a n-3 Fatty Acid

The lipid used in the composition of the present invention essentially contains a n-3 fatty acid. The "n-3 fatty acid" in the present specification means an unsaturated fatty acid having a double bond at the third carbon atom from the terminal methyl group of the hydrocarbon chain, and specific examples thereof include eicosapentaenoic acid, docosahexaenoic acid, α-linolenic acid, docosapentaenoic acid and the like. The n-3 fatty acid used in the composition of the present invention is preferably eicosapentaenoic acid, docosahexaenoic acid or docosapentaenoic acid, particularly preferably eicosapentaenoic acid. These n-3 fatty acids may be used alone, or two or more kinds thereof may be used in combination.

The n-3 fatty acid is abundantly contained in fats and oils such as fish oil, Japanese basil oil, flaxseed oil and the like, and n-3 fatty acid extracted and purified from these fats and oils can be used. In addition, a n-3 fatty acid produced by a method known per se (e.g., chemical synthesis method, fermentation method etc.) can also be used. A commercially available product marketed for foods can also be used. In addition, fats and oils abundantly containing n-3 fatty acid can also be used directly.

The lipid contained in the composition of the present invention may contain a n-3 fatty acid as well as other lipids. Examples of the lipid include edible vegetable oils such as cottonseed oil, sunflower oil, peanuts oil, rapeseed oil, soybean oil, safflower oil, olive oil, rice oil, corn oil, sesame oil, cacao butter and the like; edible animal oils such as beef tallow, lard, fish oil, butter, butter oil and the like; processed fat and oils such as shortening and the like; medium chain fatty acid oils such as coconut oil, palm oil, palm kernel oil and the like, and the like. These lipids may be used alone, or two or more kinds thereof may be used in combination.

The amount of n-3 fatty acid contained in the composition of the present invention is preferably not less than 20 wt %, more preferably not less than 25 wt %, particularly preferably not less than 30 wt %, relative to the total amount of lipid contained in the composition of the present invention. The upper limit of the amount of n-3 fatty acid is not particularly limited.

The amount of n-3 fatty acid contained in the composition of the present invention is generally 10 to 200 wt %, preferably 20 to 100 wt %, relative to the total amount of serine contained in the composition of the present invention, and more preferably 20 to 60 wt % to reduce oil ingestion as much as possible.

When the n-3 fatty acid contains eicosapentaenoic acid, the content of eicosapentaenoic acid relative to the total amount of n-3 fatty acid is generally 5 to 100 wt %. To suppress oil ingestion as much as possible, it is preferably 10 to 100 wt %, more preferably 50 to 100 wt %.

The total amount of lipid contained in the composition of the present invention is generally 1 to 90 wt %, preferably 5 to 85 wt %, relative to the whole composition.

The composition of the present invention can be provided as a medicament, food, and the like. When provided as a medicament, the subject of administration is, for example, a mammal (e.g., human, mouse, rat, hamster, rabbit, cat, dog, bovine, sheep, monkey etc.) and the like, preferably human. The "food" in the present specification is a concept widely encompassing those that can be ingested orally (excluding medicament), and includes drinks, seasoning, food additive and the like.

When the composition of the present invention is provided as a medicament, the dosage form thereof is not particularly limited, and may be any of oral medicament and parenteral medicament. Examples of the oral medicament include tablet, granule, powder, capsule (including soft capsule), elixir, syrup, microcapsule, drink, emulsion, suspension and the like, and examples of the parenteral medicament include skin external preparation (e.g., ointment, cream, gel, liquid, lotion, facial mask, bathing powder etc.), injection and the like. The composition can also be used in combination with analgesic (opioid central analgesic; steroid; non-steroidal anti-inflammatory analgesic and the like) commercially available at present.

When the composition of the present invention is provided as a food, the form thereof is not particularly limited, and may be, for example, powdered product, granular product, capsular product, tablet-like product, liquid product (e.g., drinks etc.), jelly-like drink, jelly-like product (e.g., jelly etc.), gum-like product, sheet-like product, solid product (e.g., snack stick, cookie etc.) and the like.

The composition of the present invention can also be provided as a food prescribed by the Ordinance of the Ministry of Health, Labour and Welfare, such as food with health claims and the like. The food with health claims also includes a food with an indication that it is used for particular applications (e.g., food for specified health uses, food with nutrient function claims etc.). In addition, the composition of the present invention can also be utilized as a food supplement. The food supplement here refers to those that are ingested for the purpose of supplementing nutrition besides those ingested as foods, and examples thereof include nutritional supplements and supplements (e.g., dietary supplements, etc.).

Serine and the n-3 fatty acid, which are active ingredients of the composition of the present invention, can be each singly or combinedly contained in plural (two or more) compositions. The plural compositions may be, for example, a combination of two or more medicaments, a combination of two or more foods, a combination of one or more medicaments and one or more foods, and the like.

When serine and the n-3 fatty acid are contained in plural compositions, the amount of serine relative to the total amount of amino acid, the amount of n-3 fatty acid relative to the total amount of lipid, the content of eicosapentaenoic acid relative to the total amount of n-3 fatty acid and the like are calculated from the total amount of each component contained in the plural compositions.

The composition of the present invention may contain carriers conventionally used in the field of medicament or food as necessary, as long as the object of the present invention is not impaired.

When the composition of the present invention is an oral medicament, food, or the like, examples of the carrier that may be contained include binders such as tragacanth, gum arabic, cornstarch, gelatin, high molecular weight polyvinylpyrrolidone and the like; excipients such as cellulose and a derivative thereof (e.g., microcrystalline cellulose, crystalline cellulose, hydroxypropyl cellulose etc.) and the like; swelling agents such as cornstarch, pregelatinized starch, alginic acid, dextrin and the like; lubricants such as magnesium stearate and the like; flowability improving agents such as particle silicon dioxide, methyl cellulose and the like; lubricants such as glycerin fatty acid ester, talc, polyethylene glycol 6000 and the like; thickeners such as sodium carboxymethyl cellulose, carboxyvinyl polymer, xanthan gum, gelatin and the like; sweetening agents such as sucrose, lactose, aspartame and the like; flavors such as peppermint flavor, vanilla flavor, cherry flavor, orange flavor and the like; emulsifiers such as monoglyceride, polyglycerol fatty acid ester, sucrose fatty acid ester, lecithin (e.g., soybean lecithin etc.), polyoxyethylene hydrogenated castor oil, polyoxyethylene monostearic acid ester, beeswax and the like; pH adjusters such as citric acid, sodium citrate, acetic acid, sodium acetate, sodium hydroxide and the like; thickeners such as sodium carboxymethyl cellulose, carboxyvinyl polymer, xanthan gum, gelatin and the like; corrigents such as aspartame, licorice extract, saccharin and the like; antioxidants such as erythorbic acid, butylated hydroxyanisole, propyl gallate and the like; preservatives such as sodium benzoate, sodium edetate, sorbic acid, sodium sorbate, methyl paraoxybenzoate, butyl paraoxybenzoate and the like; colorants such as red iron oxide, yellow iron oxide, black iron oxide, carmine, Food Color Blue No. 1, Food Color Yellow No. 4, Food Color Red No. 2 and the like; fats and oils such as safflower oil and the like; antioxidants such as vitamin C, vitamin A, vitamin E, various polyphenol, hydroxytyrosol, antioxidant amino acid and the like; coating agents such as shellac, sugar, hydroxypropyl methylcellulose phthalate, polyacetin and the like; preservatives such as methylparaben, propylparaben and the like; various vitamins; various amino acids and the like.

When the composition of the present invention is a parenteral medicament and the like, examples of the carrier that may be contained include higher fatty acid esters such as petrolatum, liquid paraffin, isopropyl myristate, octyldodecyl myristate and the like; higher alcohols such as squalane, lanolin, cetanol and the like; grease bases such as silicone oil, oil from plant or animal and the like; lower alcohols such as ethanol and the like; polyhydric alcohols such as polyethylene glycol, propylene glycol and the like; emulsifiers or emulsion stabilizers such as α-monoglyceryl ether, lecithin, sorbitan fatty acid ester, dextrin fatty acid ester, fatty acid monoglyceride, fatty acid metal salt, magnesium sulfate and the like; aromatic; preservative; dye; thickener; antioxidant; UV defense agent; wound therapeutic agent; anti-inflammatory agent; humectant; water and the like.

The composition of the present invention can be formulated as a unit package form per single intake. In the present specification, the "unit package form per single intake" means a package form of one or more units with single intake as one unit. For the package, a packaging material and a packaging method, a filling method (e.g., divided package, stick package etc.) generally used for a package of medicament, food, and the like can be used.

In the present specification, the "single intake" is, for example, the amount of the composition to be administered at one time when the composition of the present invention is a medicament. When the composition of the present invention is a food, it is the amount of the composition ingested in one meal.

The single intake can be appropriately controlled according to the age, body weight, sex and the like of the subject who ingests.

A single intake of the composition of the present invention can be appropriately set according to the form, dosage form, ingestion subject and the like of the composition and is not particularly limited. For a general adult (body weight 60 kg), 0.2 to 12.0 g is preferable, 0.3 to 10.0 g is more preferable, and 0.5 to 8.0 g is particularly preferable. When the single intake of the composition of the present invention is within the above-mentioned range, it does not influence general meals much, and a sustained ingestion is expected.

The composition of the present invention in a unit package form per single intake preferably contains not less than 0.1 g (more preferably not less than 0.2 g, particularly preferably not less than 0.3 g) of serine in one unit. The content of serine in this case is preferably not more than 10.0 g (more preferably not more than 8.0 g, particularly preferably not more than 5.0 g) in one unit. When the content is less than 0.1 g in one unit, serine is utilized as a protein constituting component or energy source in the body and a desired effect tends to be unexpected. When the content exceeds 10.0 g in one unit, a large amount of a single amino acid is ingested, which is not very preferable from the aspect of amino acid balance.

When the composition of the present invention is in a unit package form per single intake, the content of threonine is preferably not more than 0.15 g (more preferably not more than 0.1 g, further preferably not more than 0.05 g, particularly preferably not more than 0.025 g), in one unit.

When the composition of the present invention is in a unit package form per single intake, the n-3 fatty acid is preferably contained at not less than 0.03 g (more preferably not less than 0.04 g, particularly preferably not less than 0.05 g) in one unit. In this case, the content of the n-3 fatty acid is preferably not more than 6.00 g (more preferably not more than 4.50 g, particularly preferably not more than 3.00 g) in one unit. When the content is less than 0.03 g in one unit, a desired effect tends to be not clearly expected. A content exceeding 6.00 g in one unit is not very preferable from the aspect of flavor.

When the composition of the present invention is a unit package form per single intake and the n-3 fatty acid contains eicosapentaenoic acid, it contains eicosapentaenoic acid at preferably 20 to 4000 mg, more preferably 30 to 3000 mg, particularly preferably 40 to 2000 mg, in one unit.

While the daily ingestion of serine can be appropriately set according to the age, sex, body weight, meal state and the like of the subject who ingests, it is generally 0.1 to 10.0 g, preferably 0.2 to 8.0 g, more preferably 0.3 to 5.0 g, for an ordinary adult (body weight 60 kg).

In addition, ingestion of not less than 2 g of the n-3 fatty acid per day is recommended in Japan for an ordinary adult (body weight 60 kg) based on the lipid ingestion state in the past.

Ingestion of not less than 1 g of eicosapentaenoic acid concurrently with docosahexaenoic acid per day is recommended in Japan for an ordinary adult (body weight 60 kg) based on the lipid ingestion state in the past.

The composition of the present invention is preferably ingested once to several times per day (preferably 1 to 3 times per day), so that the daily ingestion of serine, n-3 fatty acid and eicosapentaenoic acid will each fall within the above-mentioned ranges.

The ingestion period of the composition of the present invention (period of from the date of first ingestion to the date of final ingestion) is not particularly limited, and it is generally not less than 3 days, preferably not less than 1 week, more preferably not less than 4 weeks, particularly preferably not less than 8 weeks. The upper limit of the ingestion period is not particularly set.

For application of the composition of the present invention to an animal other than human, the above-mentioned single intake, content in one unit, daily intake and the like can be appropriately increased or reduced based on the above-mentioned amount for an ordinary adult, and further considering the body weight or size of the animal, or the condition, sensitivity and the like of the animal at the time of administration.

For application of the composition of the present invention to a human, the dose of each component (serine etc.) in the composition of the present invention can be determined based on the experiment results of each animal other than human.

The composition of the present invention can be produced by a method known per se in the technical field of preparation formulation (e.g., the method described in the Japanese Pharmacopoeia, 16th Edition, the method described in WO 2015/163316, the method described in US-B-2017/0035721, all of which are incorporated herein by reference in their entireties, and the like).

The composition of the present invention is useful for preventing or improving nociceptive pain. The "nociceptive pain" in the present specification refers to pain caused by damage or possible damage to tissues by noxious stimulus or inflammation.

In the present invention, pain can be classified by a method known per se or a method analogous thereto. For example, pain can be classified into nociceptive (score: 0-12 points), neuropathic (score: 19-38 points), and both (score: 13-18 points) using PainDETECT Questionnaire developed by Freynhagen et al. (Curr Med Res Opin. 2006; 22(10); 1911-20, which is incorporated herein by reference in its entirety).

The nociceptive pain that can be prevented or improved by the composition of the present invention may be acute or chronic, and the site of pain is not particularly limited. For example, joints of neck (e.g., facet joint of cervical spine, etc.), waist (e.g., lumbar facet joint, sacroiliac joint, etc.), backbone (e.g., spinal facet joint, etc.), knee (e.g., knee joint, etc.), shoulder (e.g., scapula, shoulder joint, etc.) and the like; muscles such as skeletal muscle, smooth muscle and the like; internal organs such as stomach, intestine, liver, kidney and the like; limbs such as finger, palm of hand, back of hand, toe, sole of foot, instep of foot and the like; skin (including mucosa); bone; tooth and the like can be mentioned. The cause of nociceptive pain (injury, disease etc.) is not particularly limited and, for example, bruise, bone fracture, burn, osteoarthritis, rheumatoid arthritis, stiff neck, tenosynovitis and the like can be mentioned. The nociceptive pain that can be prevented or improved by the composition of the present invention may be accompanied by stiffness, swelling and other symptoms.

In the present specification, the "prevention" of nociceptive pain means prevention (including prevention of recurrence) of the perception of pain in individuals who have not perceived nociceptive pain. In addition, the "prevention" of nociceptive pain also includes prevention (including prevention of recurrence) of the manifestation of symptoms associated with nociceptive pain (e.g., stiffness, swelling, etc.) in individuals who have not exhibited the symptoms.

In the present specification, the "improvement" of nociceptive pain means reducing the intensity of pain, or preventing or delaying an increase in the intensity of pain in individuals who are perceiving nociceptive pain. In addition, the "improvement" of nociceptive pain also includes reducing the symptoms associated with nociceptive pain (e.g., stiffness, swelling, etc.) or preventing or delaying the exacerbation of the symptoms in individuals exhibiting the symptoms.

The composition of the present invention is preferably used for preventing or improving nociceptive pain in a joint or limb, more preferably used for preventing or improving nociceptive pain in a joint, and particularly preferably used for preventing or improving nociceptive pain in the waist or knee.

As shown in the below-mentioned Example, the composition of the present invention is also useful for preventing or improving a decrease in Quality of Life ("QOL") associated with nociceptive pain, and can be provided as a composition for preventing or improving a decrease in QOL associated with nociceptive pain.

A specific embodiment of a decrease in QOL associated with nociceptive pain is, for example, that nociceptive pain makes it difficult to perform at least one action selected from the group consisting of physically intense activities (e.g., exercise, labor, etc.), carrying of objects (e.g., carrying of heavy object, etc.), walking, stepping stairs, standing up, crouching, bending, and kneeling. The composition of the present invention is useful for improving or preventing, for example, difficulty in performing at least one action selected from the group consisting of physically intense activities, carrying of objects, walking, stepping stairs, standing up, crouching, bending, and kneeling, and the like.

In the present specification, the "prevention" of a decrease in QOL associated with nociceptive pain means preventing a decrease in QOL associated with the occurrence of nociceptive pain by preventing the perception of nociceptive pain in individuals who have not perceived nociceptive pain.

In the present specification, the "improvement" of a decrease in QOL associated with nociceptive pain means improving QOL, maintaining QOL, or reducing or delaying a decrease in QOL in individuals who are perceiving nociceptive pain.

The preventive or improving effect of nociceptive pain and the preventive or improving effect of a decrease in QOL associated with nociceptive pain according to the present invention may be evaluated by a method known per se, and the evaluation is not particularly limited. For example, the evaluation can be performed by questionnaire survey and the like using questionnaires. The questionnaire survey can be performed by a method known per se. For example, the score of each item of the questionnaires is measured before ingesting the test sample and after ingesting the test sample continuously for a certain period (e.g., 1 week to 8 weeks), and when the score after ingestion of the test sample significantly increased or tended to increase as compared with that before ingestion, the nociceptive pain can be evaluated to have been prevented or improved and the like. Examples of the questionnaire that can be used for the evaluation of the effects of the present invention include Knee Injury and Osteoarthritis Outcome Score (KOOS) and its Japanese version (J-KOOS), Japanese Orthopaedic Association Back Pain Evaluation Questionnaire (JOABPEQ), SF-36 (registered trade mark) (Medical outcomes study 36-Item Short-Form Health Survey), all of which are incorporated herein by reference in their entireties, questionnaires similar to these, and the like.

When conducting a questionnaire survey using KOOS, J-KOOS, or a questionnaire similar thereto, the composition of the present invention can significantly improve, or can achieve an improving tendency of, the score of one or more items selected from the group consisting of items relating to "stiffness; pain", items relating to "function" and items relating to "quality of life".

When conducting a questionnaire survey using JOABPEQ or a questionnaire similar thereto, the score of one or more items selected from the group consisting of items relating to "strength of low back pain", items relating to "physical function", items relating to "walking/movement", items relating to "daily role/social life", and items relating to "vitality/mentality" can be significantly improved or show an improving tendency.

When conducting a questionnaire survey using SF-36 or a questionnaire similar thereto, the composition of the present invention can significantly improve, or can achieve an improving tendency of, the score of one or more items selected from the group consisting of items relating to "physical function", items relating to "bodily pain", items relating to "vitality" and items relating to "role emotional".

The present invention also provides a method for preventing or improving nociceptive pain, including administering an effective amount of the composition of the present invention to a subject in need thereof. The present invention also provides a method for preventing or improving nociceptive pain, which includes administering an effective amount of serine and a n-3 fatty acid to a subject in need thereof.

The present invention also provides a method for preventing or improving a decrease in QOL associated with nociceptive pain, which includes administering an effective amount of the composition of the present invention to a subject in need thereof. The present invention also provides a method for preventing or improving a decrease in QOL associated with nociceptive pain, which includes administering an effective amount of serine and a n-3 fatty acid to a subject in need thereof.

These methods may exclude a medical practice. The "medical practice" here means an act of treating, operating on or diagnosing human, which is performed by physicians or dentists, or under instruction and supervision of physicians or dentists.

Other features of the invention will become apparent in the course of the following descriptions of exemplary embodiments which are given for illustration of the invention and are not intended to be limiting thereof.

EXAMPLES

In the following Examples, "%" means "wt %", unless otherwise specified.

Selection of Subjects

A questionnaire survey using PainDETECT Questionnaire was conducted on 57 adult men and women with pain, numbness, and discomfort in joint, limb, and the like, and 14 subjects (7 females and 7 males) whose scores were within the range of 0 to 12 were selected as subjects having nociceptive pain. The age, height and body weight of the test subjects were respectively 54.1±11.8 years old, 163.6±7.4 cm and 67.0±11.4 kg (each average±standard deviation).

Production of Test Sample

As a test sample, the following capsule was produced by a conventional method.

shape: OVAL-6 soft capsule (brown)

capsule specification: sodium phosphate-free vegetable-coated soft capsule (manufactured by Catalent Japan K.K., Vegicaps (registered trade mark))

composition: containing components listed in the following Table 2 in one capsule (total amount: 344 mg). In the Table, "EPA-28" is refined fish oil containing 28% of eicosapentaenoic acid and also containing 12% of docosahexaenoic acid (manufactured by Nippon Suisan Kaisha, Ltd.).

TABLE 2

| component | content (mg) |
|---|---|
| L-serine | 156.24 |
| EPA-28 | 156.24 |
| safflower oil | 8.50 |

TABLE 2-continued

| component | content (mg) |
|---|---|
| beeswax | 22.02 |
| soybean lecithin | 1.00 |

Test Method

Each test subject ingested the test sample once per day for 8 weeks. The ingestion amount of the test sample was 4 capsules once per day. The ingestion method was oral ingestion with water before bedtime at least 2 hr after dinner. When ingestion before bedtime was difficult, the test sample was orally ingested after 2 hr or more from the meal, and no meal was taken for at least 2 hr after the ingestion.

A questionnaire survey regarding knee condition, waist condition and health-related QOL was conducted for each subject 1 week before the start of ingestion of the test sample, the date of start of ingestion, 1 week, 4 weeks and 8 weeks after the start of ingestion. In the questionnaire survey on the knee condition, a questionnaire (J-KOOS improved version) modified in 25 items regarding "stiffness; pain", "function", and "quality of life" based on all 42 items of J-KOOS was used. In the questionnaire survey on the waist condition, a questionnaire in which the way JOABPEQ is scored was changed and the questions about the degree of pain and numbness were removed (JOABPEQ improved version) was used. In the questionnaire survey on the health-related quality of life, a questionnaire in which the way SF-36 is scored was changed (SF-36 improved version) was used.

Evaluation

The score of each questionnaire was calculated 1 week before the start of ingestion of the test sample, the date of start of ingestion, 1 week, 4 weeks and 8 weeks after the start of ingestion, the average of the score one week before the start of ingestion of the test sample and the score on the date of start of the ingestion was set as the "baseline", and the scores 1 week, 4 weeks and 8 weeks after the start of ingestion were each compared with the baseline.

The results are shown in the following Table 3 (results of questionnaire survey using J-KOOS improved version), Table 4 (results of questionnaire survey using JOABPEQ improved version) and Table 5 (results of questionnaire survey using SF-36 improved version).

TABLE 3

| Results questionnaire survey using J-KOOS improved version | | | | |
|---|---|---|---|---|
| | baseline (average of one week before start of ingestion and date of start of ingestion) | one week after start of ingestion | 4 weeks after start of ingestion | 8 weeks after start of ingestion |
| total score of all items | 112.6 ± 11.2 | 116.4 ± 8.3 ** | 117.7 ± 7.9 ** | 118.6 ± 8.7 ** |
| total score of items relating to "stiffness; pain" | 29.4 ± 4.0 | 30.8 ± 3.5 ** | 31.6 ± 3.3 *** | 32.4 ± 3.0 *** |
| total score of items relating to "function" | 69.1 ± 6.6 | 70.9 ± 4.6 * | 71.4 ± 4.6 * | 71.5 ± 5.7 * |
| total score of items relating to "quality of life" | 14.1 ± 1.0 | 14.7 ± 0.6 * | 14.7 ± 0.5 * | 14.8 ± 0.4 * | mean ± SD

* $p < 0.05$,  $p < 0.01$, * $p < 0.001$ (paired t-test)

As is clear from the results shown in Table 3, the total score of all items significantly increased from 1 week to 8 weeks after the start of ingestion of the test sample as compared with the baseline.

In addition, the total score of the items relating to "stiffness, pain", the total score of the items relating to "function", and the total score of the items relating to "quality of life" significantly increased from 1 week to 8 weeks after the start of ingestion of the test sample as compared to the baseline.

From these results, it was suggested that the combination of serine and a n-3 fatty acid is useful for preventing and improving nociceptive pain (particularly, nociceptive pain in the knee).

TABLE 4

Results questionnaire survey using JOABPEQ improved version

|  | baseline (average of one week before start of ingestion and date of start of ingestion) | one week after start of ingestion | 4 weeks after start of ingestion | 8 weeks after start of ingestion |
|---|---|---|---|---|
| total score of all items | 103.0 ± 12.3 | 110.0 ± 11.8 *** | 108.7 ± 12.1 * | 111.9 ± 9.9 *** |
| total score of items relating to "strength of low back pain" | 16.1 ± 2.6 | 16.9 ± 2.5 # | 17.0 ± 2.4 | 17.7 ± 2.6 # |
| total score of items relating to "physical function" | 26.9 ± 3.2 | 28.1 ± 3.9 * | 27.8 ± 4.1 | 28.4 ± 3.5 ** |
| total score of items relating to "walking/movement" | 21.5 ± 4.4 | 23.6 ± 3.3 ** | 22.9 ± 3.7 # | 23.4 ± 2.7 * |
| total score of items relating to "daily role/social life" | 13.3 ± 1.7 | 14.1 ± 1.5 ** | 14.1 ± 1.5 * | 14.4 ± 0.9 * |
| total score of items relating to "vitality/mentality" | 25.3 ± 2.7 | 27.3 ± 3.3 ** | 27.0 ± 2.9 * | 27.9 ± 2.9 ** | mean ± SD
$p < 0.1$, * $p < 0.05$,  $p < 0.01$, * $p < 0.001$ (paired t-test)

As is clear from the results shown in Table 4, the total score of all items significantly increased from 1 week to 8 weeks after the start of ingestion of the test sample as compared with the baseline.

In addition, the total score of the items relating to "physical functions", the total score of the items relating to "walking/movement", the total score of the items relating to "daily role/social life", and the total score of the items relating to "vitality/mentality" each significantly increased from 1 week to 8 weeks after the start of ingestion of the test sample as compared to the baseline. The total score of the items relating to "strength of low back pain" tended to increase as compared to the baseline.

From these results, it was suggested that the combination of serine and a n-3 fatty acid is useful for preventing and improving nociceptive pain (particularly, nociceptive pain in the waist).

TABLE 5

Results questionnaire survey using SF-36 improved version

|  | baseline (average of one week before start of ingestion and date of start of ingestion) | one week after start of ingestion | 4 weeks after start of ingestion | 8 weeks after start of ingestion |
|---|---|---|---|---|
| total score of all items | 145.7 ± 14.9 | 151.9 ± 12.9 ** | 152.6 ± 12.3 * | 153.2 ± 10.6 * |
| total score of items relating to "physical function" | 41.8 ± 6.0 | 43.9 ± 4.9 * | 44.0 ± 5.9 * | 45.2 ± 4.5 ** |
| total score of items relating to "bodily pain" | 7.9 ± 0.9 | 8.9 ± 1.2 *** | 8.6 ± 1.3 # | 8.8 ± 1.4 * |
| total score of items relating to "vitality" | 13.5 ± 2.3 | 14.1 ± 2.0 # | 14.5 ± 2.0 * | 14.8 ± 2.0 ** |
| total score of items relating to "role emotional" | 13.7 ± 1.4 | 14.4 ± 1.3 # | 14.6 ± 0.9 # | 14.6 ± 0.9 # | mean ± SD
$p < 0.1$, * $p < 0.05$,  $p < 0.01$, * $p < 0.001$ (paired t-test)

As is clear from the results shown in Table 5, the total score of all items was significantly increased from 1 week to 8 weeks after the start of ingestion of the test sample as compared with the baseline.

In addition, the total score of the items relating to "physical functions", and the total score of the items relating to "bodily paint" significantly increased from 1 week to 8 weeks after the start of ingestion of the test sample as compared to the baseline. The total score of the items relating to "vitality" significantly increased from 4 weeks to 8 weeks after the start of ingestion of the test sample as compared to the baseline. The total score of the items relating to "role emotional" tended to increase from 1 week to 8 weeks after the start of ingestion of the test sample as compared to the baseline.

From these results, it was suggested that the combination of serine and n-3 fatty acid improve QOL (physical functions, bodily pain, vitality, role emotional) by preventing or improving nociceptive pain.

INDUSTRIAL APPLICABILITY

According to the present invention, a composition for preventing or improving nociceptive pain can be provided.

According to the present invention, a composition for preventing or improving a decrease in QOL associated with nociceptive pain can be provided.

Since the composition contains serine and n-3 fatty acid with established safety as active ingredients, it can be ingested safely for a long term.

The invention claimed is:

1. A method for treating chronic nociceptive pain in a subject in need thereof, the method comprising administering to the subject a therapeutically effective amount of a composition comprising one or more amino acids and one or more n-3 fatty acids, wherein the one or more amino acids comprises serine in an amount that is at least 50 wt % relative to the total amount of amino acid, and the one or more n-3 fatty acids comprises eicosapentaenoic acid in an amount that is at least 20 wt % relative to the total amount of n3 fatty acid.

2. The method according to claim 1, wherein said one or more n-3 fatty acids further comprises one or more selected from the group consisting of docosapentaenoic acid and docosahexaenoic acid.

3. The method according to claim 1, wherein said composition has a unit package form per single intake, and comprises not less than 0.1 g of serine in one unit, and not less than 0.03 g of said at least one n-3 fatty acid in one unit.

4. The method according to claim 1, wherein said nociceptive pain is a nociceptive pain in a joint or limb.

5. The method according to claim 1, wherein said composition is a medicament or food.

* * * * *